(12) United States Patent
Siltanen et al.

(10) Patent No.: US 7,813,469 B2
(45) Date of Patent: Oct. 12, 2010

(54) METHOD FOR PRODUCING A THREE-DIMENSIONAL DIGITAL X-RAY IMAGE

(75) Inventors: Samuli Siltanen, Helsinki (FI); Petri Jouhikainen, Järvenpää (FI)

(73) Assignee: GE Healthcare Finland Oy (FI)

( * ) Notice: Subject to any disclaimer, the term of this patent is extended or adjusted under 35 U.S.C. 154(b) by 247 days.

(21) Appl. No.: 11/631,228

(22) PCT Filed: Jul. 1, 2004

(86) PCT No.: PCT/FI2004/000417

§ 371 (c)(1),
(2), (4) Date: Sep. 5, 2008

(87) PCT Pub. No.: WO2006/003235

PCT Pub. Date: Jan. 12, 2006

(65) Prior Publication Data

US 2009/0041178 A1   Feb. 12, 2009

(51) Int. Cl.
*A61B 6/00* (2006.01)
(52) U.S. Cl. .............................. 378/4; 378/38
(58) Field of Classification Search .................. 378/4, 378/37, 38, 39
See application file for complete search history.

(56) References Cited

U.S. PATENT DOCUMENTS

| 4,903,204 | A | * | 2/1990 | Dobbins, III | 382/255 |
|---|---|---|---|---|---|
| 5,214,686 | A | * | 5/1993 | Webber | 378/38 |
| 5,511,106 | A | | 4/1996 | Doebert et al. | |
| 6,256,370 | B1 | * | 7/2001 | Yavuz | 378/22 |
| 6,611,575 | B1 | | 8/2003 | Alyassin et al. | |
| 6,707,878 | B2 | * | 3/2004 | Claus et al. | 378/22 |
| 6,850,589 | B2 | * | 2/2005 | Heumann et al. | 378/19 |
| 2001/0038678 | A1 | * | 11/2001 | Grass et al. | 378/4 |
| 2003/0194049 | A1 | * | 10/2003 | Claus et al. | 378/22 |
| 2004/0066877 | A1 | * | 4/2004 | Arai et al. | 378/4 |
| 2006/0239400 | A1 | * | 10/2006 | Sukovic et al. | 378/38 |

OTHER PUBLICATIONS

International Search Report dated Feb. 11, 2005.
Written Opinion dated Feb. 11, 2005.

* cited by examiner

*Primary Examiner*—Edward J Glick
*Assistant Examiner*—Alexander H Taningco
(74) *Attorney, Agent, or Firm*—Andrus, Sceales, Starke & Sawall, LLP

(57) ABSTRACT

The present invention relates to a method for producing a three-dimensional digital x-ray image by using digital x-ray images taken of the object from at least two different directions as input for a reconstruction algorithm. In the method, at least one of the images used as input is taken as a tomosynthetic slice image of a region of interest (5) in the object (3) of imaging.

10 Claims, 2 Drawing Sheets

US 7,813,469 B2

METHOD FOR PRODUCING A THREE-DIMENSIONAL DIGITAL X-RAY IMAGE

CROSS REFERENCE TO RELATED APPLICATION

The present application is the U.S. national stage application of International Application PCT/FI2004/000417, filed Jul. 1, 2004, which international application was published on Jan. 12, 2006, as International Publication WO 2006/003235.

BACKGROUND OF THE INVENTION

The invention relates to a method for producing a three-dimensional (3D) digital x-ray image by using digital x-ray images taken of the object from at least two different directions as input for a reconstruction algorithm. A reconstruction algorithm refers to an algorithm by means of which two-dimensional or three-dimensional x-ray image information on the object being imaged is reconstructed, that is, produced.

Conventionally, the input used for a reconstruction algorithm in 3D x-ray imaging consists of a selection of projections taken from different directions, giving as a result a three-dimensional voxel representation of the tissue being imaged. For example, U.S. Pat. No. 6,611,575 B1 (Assignee General Electric Company) describes three-dimensional imaging using projections taken from different directions as a starting point, the projections being entered in the reconstruction algorithm in the form of spaced-apart planar images. These planar Images are then used as input for the chosen 3D imaging method. The imaging method may be, for example, Volume Rendering or Surface Rendering or a combination of the two.

It is often necessary to select a region of interest (ROI) within the object and to image each projection so that only the ROI is shown in the image. Reasons for this are the minimization of the radiation dosage and the size limitations of the detector. This type of 3D imaging is called local tomography. The problem with local tomography is that objects at a distance from the ROI can be seen in the projections and cause artifacts (errors due to calculation) in the reconstruction.

A technique long since known by dentists and based on simple local tomography is tomosynthetic imaging, in which a two-dimensional slice inside a tissue is imaged accurately and areas at a distance from the slice are shown unclearly. Tomosynthetic slice images can be produced by any of the following methods:
a) By moving the film/detector and radiation source during imaging, which blurs objects at a distance from the in-focus plane and images objects on the in-focus plane sharply.
b) By taking a series of static images, which are appropriately moved and summed to produce slice images corresponding approximately to those produced under a).
c) By combining a) and b): a series of slightly blurred slice images complying with a) are taken, which are then moved and summed according to b).

SUMMARY OF THE INVENTION

The aim of the present invention is to provide a method by means of which the artefacts in a tomographic 3D image can be eliminated and, in addition, the Image quality be improved in areas where conventional 3D imaging based on projection imaging is insufficient, for example, in longitudinal imaging of the jaw bone. To achieve this aim, the method according to the invention is characterised in that in the method, at least one of the images used as input in the method is taken as a tomosynthetic slice image of a region of interest in the object of imaging.

BRIEF DESCRIPTION OF THE DRAWINGS

The Invention is described in greater detail in the following, with reference to the accompanying drawings, in which.

DETAILED DESCRIPTION OF THE INVENTION

Figure 1:
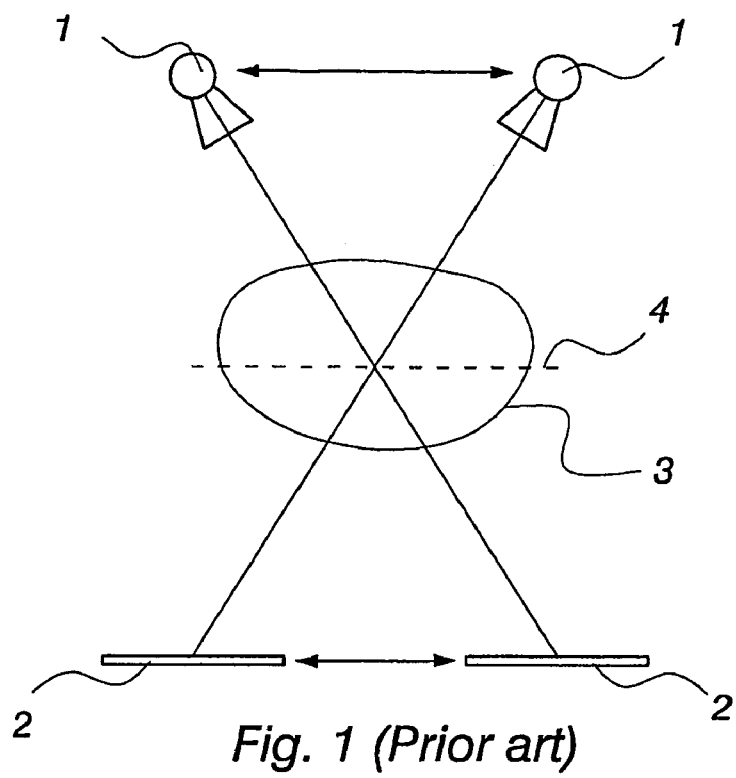
FIG. 1 shows a diagrammatic view in principle of the implementation of tomosynthetic imaging.
Figure 2:
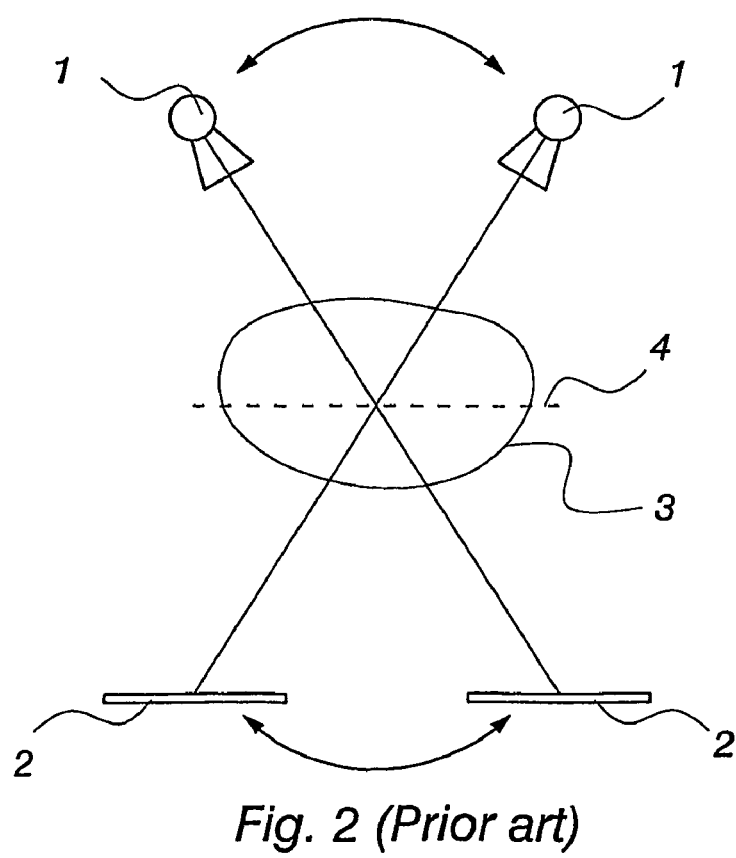
FIG. 2 shows a diagrammatic view in principle of another implementation of tomosynthetic imaging.

FIG. 1 shows diagrammatically the principle of conventional tomosynthetic imaging. Reference numeral 1 denotes the x-ray source, reference numeral 2 the detector receiving the radiation that has passed through the object of imaging 3, and reference numeral 4 the in-focus plane. Moving the radiation source 1 and the detector 2 simultaneously, at the same speed, in opposite directions will produce sharp image areas on the in-focus plane 4, whereas distant objects become blurred. FIG. 2 shows another conventional method for implementing tomosynthetic imaging. In this method, the x-ray source 1 and the detector 2 are at a fixed distance from one another, turning as an integrated unit around the in-focus plane 4.

Figure 3:
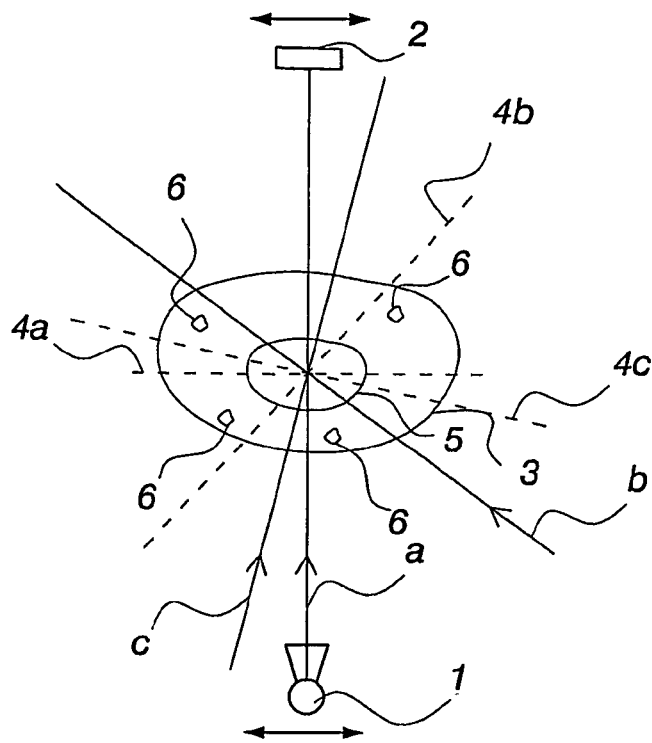
FIG. 3 shows a diagrammatic view in principle of an implementation of the method according to the invention.
Figure 4:
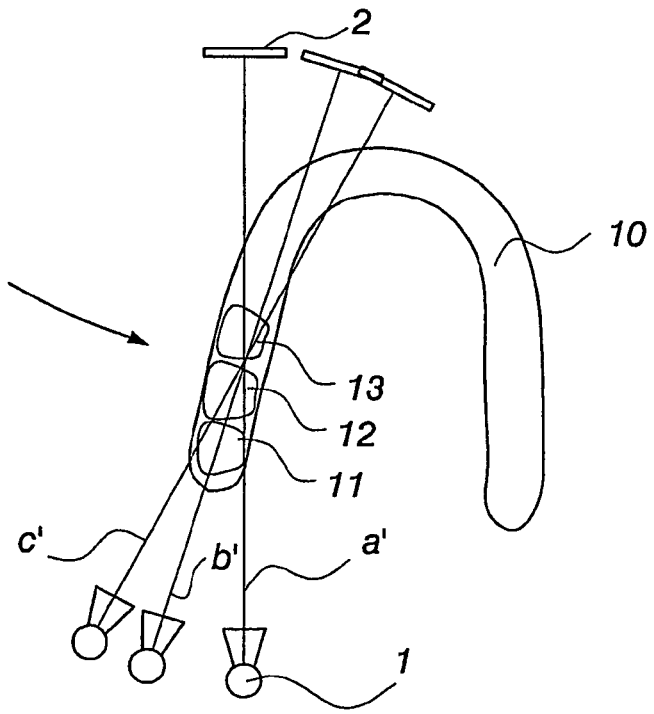
FIG. 4 shows a diagrammatic view of an alternative implementation of the disclosed method.

FIG. 3 shows diagrammatically a method of implementation according to the invention. Of the region of interest 5 inside the object 3 being imaged is first taken—for example from three directions a, b and c—a tomosynthetic slice image along the corresponding in-focus planes 4a, 4b and 4c, which slice images are then used as input for a tomographic, 3D reconstruction algorithm. A tomosynthetic slice image means, for example, a projection. Objects 6 outside the region 5 are blurred out of the images. Slice images can be taken from various directions and as input for a reconstruction algorithm can also be used projections taken from one or more different directions. FIG. 4 shows diagrammatically the imaging of the longitudinal slices of the jaw bone. Here, projections of the jaw bone 10 are taken longitudinally and in directions a', b' and c' deviating slightly from it. Of the data obtained is produced, for example, a TACT (Tuned-aperture computed tomography) or ART (Algebraic Reconstruction Technique) reconstruction.

Since this is limited angle tomography, the resolution of the reconstruction is poor in the longitudinal direction of the jaw bone, which means that, for example, the gaps between the teeth 11-13 will not appear clearly from the images. By also taking tomosynthetic slice images or, for example, a short panoramic slice, at a 90 degree angle with respect to the directions of projection imaging, and by using them as input for the reconstruction algorithm together with projections, image quality can be improved substantially, whereby, for example, the gaps between teeth will be clearly shown in the images.

The method according to the invention can be used with any digital x-ray machine, such as a panoramic machine, mammography machine, an intra-oral machine or a surgical C arc. When taking projections with a device revolving around the object being imaged, the device having an x-ray source in one arm and a detector receiving x-radiation in the other arm opposite the object being imaged, it is possible to take images while the machine is moving, instead of static projections. This allows for the imaging speed to be increased, because the machine does not need to be stopped during imaging, and also objects at a distance from the region of interest are blurred. The degree of blurring can be adjusted with the exposure time and the speed of rotation. A longer exposure time can be used if necessary, which will reduce the power requirement of the x-ray source.

The invention claimed is:

1. A method for producing a three-dimensional digital x-ray image by using digital x-ray images taken of an object from at least two different directions as input for a reconstruction algorithm, wherein, at least one of the images used as an input is a tomosynthetic slice image of a region of interest in the object of imaging, wherein the tomosynthetic slice image comprises a sharp image layer, and a blurred image layer and the reconstruction algorithm produces the three-dimensional digital x-ray image of the region of interest using both the sharp image layer and the blurred image layer.

2. A method as claimed in claim 1, wherein the tomosynthetic slice image comprises a linear, sharply imaged layer.

3. A method as claimed in claim 1, wherein the tomosynthetic slice image comprises a curved, sharply imaged layer.

4. A method as claimed in claim 1, wherein, the tomosynthetic slice image is a projection from an x-ray device comprising an x-ray source and a detector that receives radiation, wherein the x-ray device is rotated around a fulcrum, and that an exposure of the at least one image is performed during the rotary movement.

5. A method of producing a three-dimensional digital x-ray image of an object, the method comprising:
acquiring a first digital x-ray image of a region of interest in the object from a first direction wherein the first digital x-ray image is a tomosynthetic slice image;
acquiring a second digital x-ray image of the region of interest in the object from a second direction; and
using the first and second digital x-ray images as inputs for a reconstruction algorithm to produce a three-dimensional digital x-ray image;
wherein the first digital x-ray tomosynthetic slice image comprises an in-focus plane comprising the region of interest and a blurred plane outside the region of interest.

6. The method of claim 5, wherein an object outside of the region of interest is blurred out of the three-dimensional digital x-ray image.

7. The method of claim 5, further comprising adjusting an exposure time for the first digital x-ray image to adjust the degree of blurring of the blurred plane.

8. The method of claim 7, further comprising adjusting a speed of rotation when acquiring the first digital x-ray image to adjust the degree of blurring of the blurred plane.

9. The method of claim 5, further comprising:
moving a detector and a radiation source while acquiring the first digital x-ray image, wherein the movement focuses an object in an in-focus plane and blurs an object outside of the in-focus plane.

10. The method of claim 9, further comprising:
summing the first and second digital x-ray images to produce the three-dimensional digital x-ray image.

* * * * *